United States Patent
Wright et al.

(10) Patent No.: US 11,673,592 B2
(45) Date of Patent: Jun. 13, 2023

(54) CART FOR MEDICAL EQUIPMENT

(71) Applicant: Covidien LP, Mansfield, MA (US)

(72) Inventors: Mark Wright, Carlsbad, CA (US);
Matthew Phillips, Carlsbad, CA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 17/573,763

(22) Filed: Jan. 12, 2022

(65) Prior Publication Data

US 2022/0135099 A1 May 5, 2022

Related U.S. Application Data

(63) Continuation of application No. 16/804,886, filed on Feb. 28, 2020, now Pat. No. 11,254,340.

(60) Provisional application No. 62/819,280, filed on Mar. 15, 2019.

(51) Int. Cl.
*B62B 3/04* (2006.01)
*B62B 3/02* (2006.01)
*B62B 5/06* (2006.01)

(52) U.S. Cl.
CPC ............ *B62B 3/04* (2013.01); *B62B 3/02* (2013.01); *B62B 5/06* (2013.01); *B62B 2202/56* (2013.01)

(58) Field of Classification Search
CPC .... B62B 3/04; B62B 3/02; B62B 5/06; B62B 2202/56
See application file for complete search history.

(56) References Cited

U.S. PATENT DOCUMENTS

| | | | |
|---|---|---|---|
| D500,575 S * | 1/2005 | Lucas | D34/12 |
| 6,980,419 B2 * | 12/2005 | Smith | G01S 7/52082 361/679.41 |
| D544,962 S * | 6/2007 | Diener | D24/186 |
| 7,594,668 B2 * | 9/2009 | Arceta | A61G 12/001 280/47.35 |
| D613,866 S * | 4/2010 | Tanaka | D24/185 |
| D652,521 S * | 1/2012 | Ross | D24/185 |
| D652,936 S * | 1/2012 | Ross | D24/185 |
| 8,240,684 B2 * | 8/2012 | Ross | A61M 16/021 280/79.11 |
| D712,540 S * | 9/2014 | Hansen | D24/158 |
| D762,339 S * | 7/2016 | McRorie | D34/27 |
| 9,457,828 B1 * | 10/2016 | Guirlinger | B62B 3/04 |
| D824,521 S * | 7/2018 | Adams | D24/158 |
| 10,137,916 B1 * | 11/2018 | Glassberg | B62B 3/102 |
| D863,559 S * | 10/2019 | Brooks | D24/185 |
| 10,453,572 B1 * | 10/2019 | Brooks | G16H 40/40 |
| D866,110 S * | 11/2019 | D'Almada | D34/21 |
| D911,529 S * | 2/2021 | Meurer | D24/185 |
| 2010/0032927 A1 * | 2/2010 | Gordon | A47B 3/10 280/659 |

(Continued)

*Primary Examiner* — Erez Gurari

(57) ABSTRACT

A cart for medical equipment includes a column supporting a platform for mounting a piece of medical equipment to the cart. A base including one or more wheels that support the column, and a handgrip at least partially encircling the platform. The handgrip includes an upper surface substantially devoid of openings and an opposite lower surface including one or more elongated accessory slots opening downwardly toward the one or more wheels. The one or more elongated accessory slots are configured to receive a portion of an accessory mount such that the accessory mount is slidingly adjustable along a length of the one or more accessory slots.

20 Claims, 7 Drawing Sheets

(56) References Cited

U.S. PATENT DOCUMENTS

| | | | |
|---|---|---|---|
| 2010/0213679 A1* | 8/2010 | Smith | B62B 3/10 |
| | | | 280/727 |
| 2012/0236496 A1* | 9/2012 | McRorie | F16M 13/00 |
| | | | 361/679.55 |
| 2013/0307236 A1* | 11/2013 | Lu | B62B 3/02 |
| | | | 280/35 |
| 2015/0105660 A1* | 4/2015 | Ninomiya | A61B 8/4427 |
| | | | 600/437 |
| 2015/0227127 A1* | 8/2015 | Miller | G16H 20/13 |
| | | | 700/244 |
| 2016/0082998 A1* | 3/2016 | Eisenhut | B62B 3/04 |
| | | | 280/47.35 |
| 2016/0303442 A1* | 10/2016 | Tran | A63B 55/30 |
| 2019/0111956 A1* | 4/2019 | Phillips | B62B 5/0461 |
| 2020/0247444 A1* | 8/2020 | Lucas | B62B 3/02 |
| 2020/0290660 A1* | 9/2020 | Wright | A61B 50/13 |
| 2021/0070338 A1* | 3/2021 | Wright | B62B 3/02 |
| 2021/0259796 A1* | 8/2021 | Danilkin | A61B 50/13 |

* cited by examiner

CART FOR MEDICAL EQUIPMENT

CROSS-REFERENCE TO RELATED APPLICATIONS

This application is a continuation of U.S. application Ser. No. 16/804,886, filed Feb. 28, 2020, which claims benefit of U.S. Provisional Patent Application No. 62/819,280, filed Mar. 15, 2019, the disclosures of which are hereby incorporated herein by reference in their entireties. To the extent appropriate a claim of priority is made to each of the above disclosed applications.

INTRODUCTION

The present disclosure relates to a cart for medical equipment. In patient care facilities such as hospitals, urgent care centers, nursing homes, surgery centers, and other similar facilities, portable carts are used to organize, store, and transport medical equipment. These carts can support life-saving medical equipment such as mechanical ventilators, resuscitation equipment, surgical tools, vital sign monitors, medication pumps, and other therapeutic medical devices. Carts also support accessories such as breathing circuits, intravenous tubing, catheters, oxygen tanks, bandages, tape, and similar items as needed by the medical caregivers. The remainder of this disclosure addresses improvements in this field.

SUMMARY

This summary is provided to introduce a selection of concepts in a simplified form that are further described below. In an aspect, the technology relates to a cart for medical equipment, including: a column supporting a platform for mounting a piece of medical equipment to the cart; a base including one or more wheels that support the column; and a handgrip at least partially encircling the platform, the handgrip includes: an upper surface substantially devoid of openings; and an opposite lower surface including one or more elongated accessory slots opening downwardly toward the one or more wheels, the one or more elongated accessory slots are configured to receive a portion of an accessory mount such that the accessory mount is slidingly adjustable along a length of the one or more accessory slots.

In an example, the one or more accessory slots are substantially T-shaped. In another example, the one or more accessory slots are substantially dovetail-shaped. In yet another example, an enlarged opening is located at an end of the one or more accessory slots, and the opening is configured to direct a portion of the accessory mount into the one or more accessory slots. In still another example, the opening is substantially tapered. In an example, the handgrip includes an unbroken loop around the platform. In another example, at least a portion of the handgrip is devoid of the one or more accessory slots. In yet another example, the handgrip is substantially rectangular and two opposing sides include a pivot point so that a portion of the handgrip may selectively pivot relative to the column.

In another aspect, the technology relates to a cart for a medical ventilator, including: a column supporting a platform for mounting at least a portion of the medical ventilator to the cart; a base including one or more wheels that support the column; a handgrip encircling the platform in an unbroken loop, wherein the handgrip includes: an upper surface; and an opposite lower surface including one or more elongated accessory slots opening downwardly toward the one or more wheels; and at least one accessory mount including a head, the head is at least partially receivable within the one or more elongated accessory slots such that the at least one accessory mount is slidingly adjustable along a length of the one or more accessory slots.

In an example, the at least one accessory mount includes a clamp for selectively locking the at least one accessory mount to the handgrip. In another example, the clamp is biased toward a tightening configuration to lock the at least one accessory mount to the handgrip. In yet another example, the at least one accessory mount supports an accessory, and the accessory includes a circuit support arm. In still another example, the one or more accessory slots includes an enlarged opening configured to receive the head so that the head can be disposed within the one or more elongated accessory slot. In an example, the upper surface includes at least one indicia that corresponds to a position of the enlarged opening.

In another aspect, the technology relates to a handgrip assembly for a medical equipment cart, including: a handgrip that at least partially encircles an upper portion of the medical equipment cart, the handgrip including: an upper surface substantially devoid of openings; and an opposite lower surface including one or more elongated accessory slots opening in a downward direction; and at least one accessory mount including a head, the head is at least partially receivable within the one or more elongated accessory slots such that the at least one accessory mount is slidingly adjustable along a length of the one or more accessory slots.

In an example, the one or more accessory slots extend around the handgrip for about 270°. In another example, the handgrip is substantially rectangular shaped, and the one or more accessory slots include three discrete accessory slots, each disposed on a separate side of the handgrip. In yet another example, the corners of the handgrip are substantially devoid of the one or more accessory slots. In still another example, each of the three accessory slots includes at least one enlarged opening configured to receive the head so that the head can be disposed within the one or more elongated accessory slots. In an example, each end of the three accessory slots includes an enlarged opening of the at least one enlarged opening.

The foregoing general description and the following Detailed Description are exemplary and explanatory and are intended to provide further explanation of the disclosure as claimed.

BRIEF DESCRIPTION OF THE DRAWINGS

The following drawing figures, which form a part of this application, are illustrative of aspects of systems and methods described below.

Figure 1:
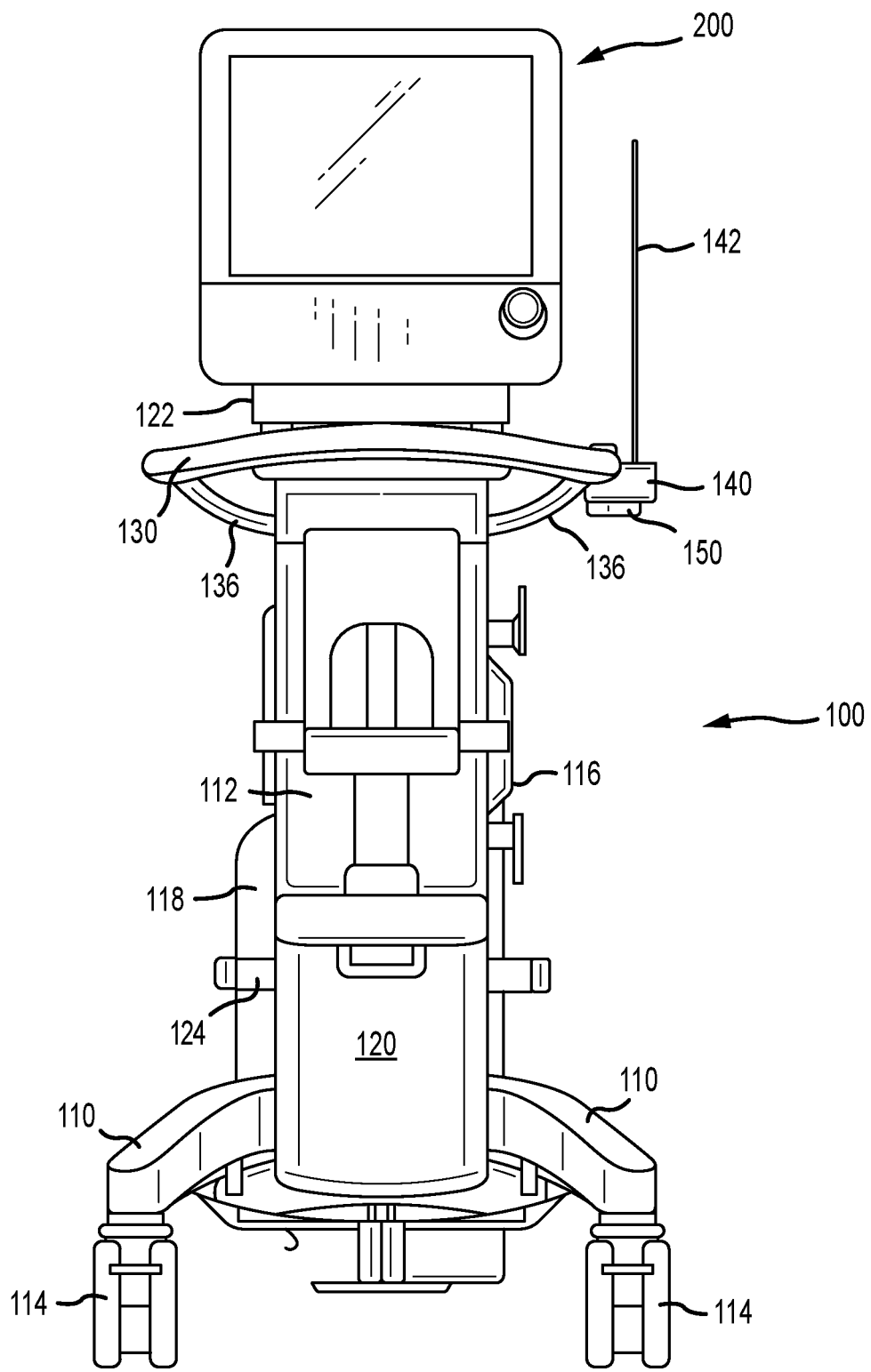
FIG. 1 is front view of a cart for medical equipment according to an embodiment of the disclosure.

Specific embodiments have been shown by way of example in the drawings and are described in detail below. The disclosure is amenable to various modifications and is intended to cover all modifications, equivalents, and alternatives falling within the scope of the disclosure and the appended claims.

DETAILED DESCRIPTION

Although the techniques introduced above and discussed in detail below may be implemented for a variety of medical devices and equipment, some examples will discuss the implementation of these techniques in the context of a medical ventilator for use in providing ventilation support to a human patient. Medical ventilators are used to provide breathing gases to patients who are otherwise unable to breathe sufficiently. A person of skill in the art will understand that the technology described in the context of a medical ventilator for human patients could be adapted for use with other medical devices or equipment.

A cart for medical equipment, such as a ventilator, is described herein. The cart includes a handgrip that extends around the cart so that the cart can be easily grasped and controlled. The handgrip also acts as a bumper so that the medical components thereon are protected from being struck during movement of the cart. In some examples, the handgrip includes two pivot points so that a portion of the handgrip may fold. This movement of the handgrip increases access to some components, such as gas tanks, for the technologist. Furthermore, the handgrip includes one or more elongated accessory slots that open in a downward direction. This orientation prevents the slot from collecting water or other fluids, while allowing the upper surface to be easily wiped clean. One or more accessory mounts can be coupled to the handgrip via the slots. Because the slots extend at least partially around the handgrip, the accessory mount can be selectively positioned at any location on the handgrip as required or desired so that the technologist can more easily customize the set-up of the medical components on the handgrip and the cart.

Figure 2:
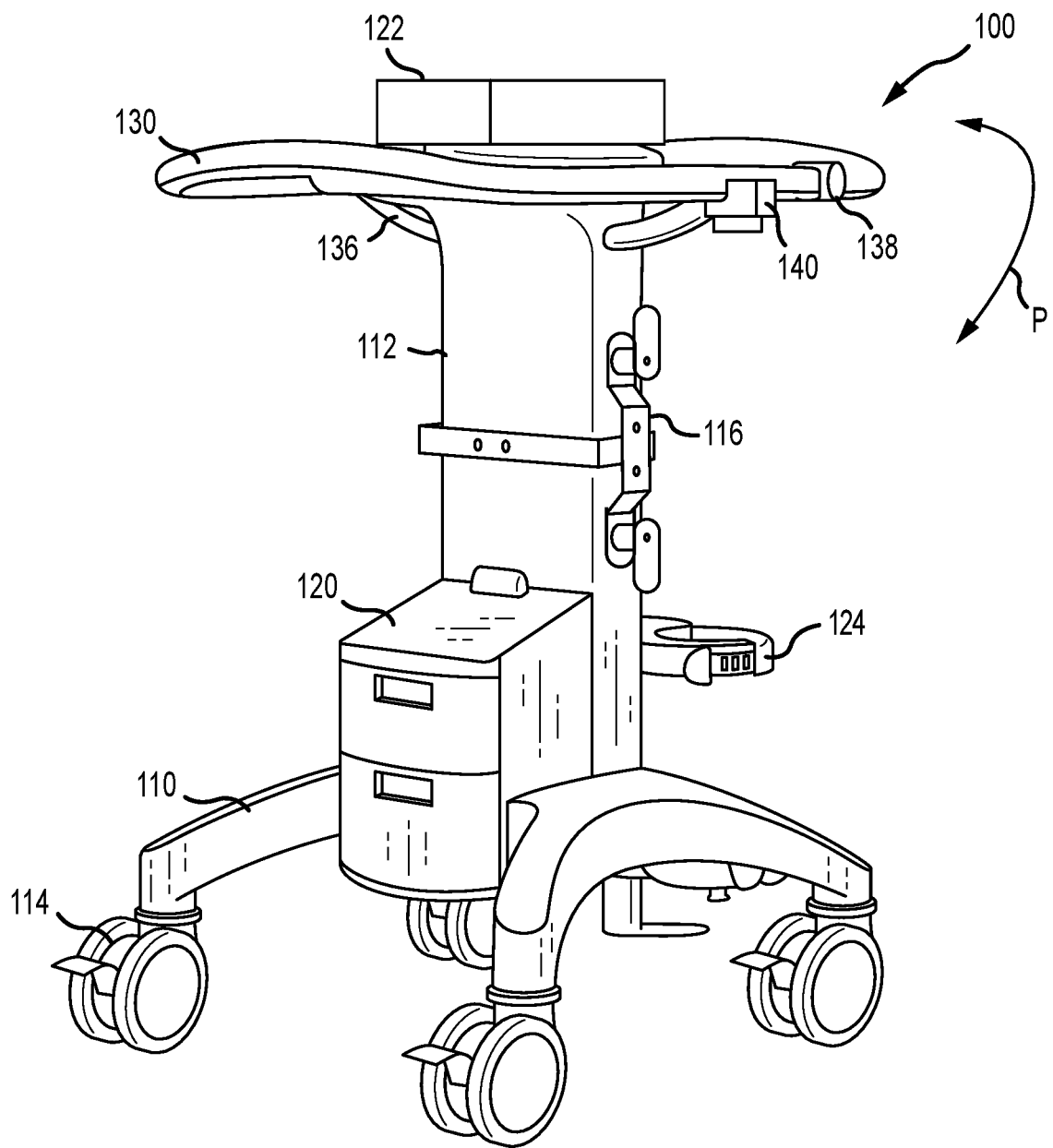
FIG. 2 is a front perspective view of the cart shown in FIG. 1.

FIG. 1 depicts a front view of a cart 100 for medical equipment according to an embodiment of the present disclosure. In the example, the cart 100 is supporting a medical ventilator 200 so that the ventilator 200 and the accompanying accessories may be transported in an efficient and organized manner around the medical care facility. The cart 100 can also support other medical accessories and/or equipment as required or desired. The cart 100 includes a base 110 that supports a column 112. The base 110 rests on a set of wheels or casters 114 that assist in moving the cart 100. The column 112 includes various brackets, clips, and hooks 116 that can hold accessories and tools. The column 112 can also include one or more drawers 120 for additional storage. For example, FIG. 1 illustrates a single drawer 120, while FIG. 2 illustrates multiple drawers 120. Additionally, a tank mount assembly 124 is mounted to the base 110 so that one or more gas tanks 118 can be mounted on the cart 100. The tank mount assembly 124 can include any number of bracket, straps, mounts, etc. to hold the tanks 118 to the cart 100.

At the top of the column 112 is a platform 122. The platform 122 is configured to support the ventilator 200 so that the ventilator 200 can be mounted on the cart 100. Also, at or near the top of the column 112 and proximate the platform 122, the cart 100 includes a handgrip 130. In the example, the handgrip 130 fully encircles the top of the column 112 and the platform 122 in an unbroken loop. One or more arms 136 extend between the column 112 and the handgrip 130, providing support of the handgrip 130 in a position away from the column 112. The handgrip 130 enables for easy grasping and control of the cart 100 from any side of the cart 100 (e.g., the front, either side, or the back). In one example, a technologist may use the handgrip 130 to guide the cart 100 around the medical care facility. In another example, a patient may use the handgrip 130 for assistance while standing. In the example, the handgrip 130 may be shaped without any sharp corners so as to prevent the handgrip 130 from being caught on other surfaces or objects. The handgrip 130 is larger in perimeter size than the column 112 and/or platform 122, thereby reducing the likelihood that the ventilator 200 and/or any other medical compartment will be struck by movement of the cart 100. In other example, the handgrip 130 may be segmented and extend at least partially around the upper portion of the cart 100.

Additionally, the handgrip 130 can also be used to support one or more accessory mounts 140. The accessory mount 140 is configured to be selectively coupled to the handgrip 130 as described further herein, and itself is used to support various medical accessories, such as a pole 142 (e.g., an IV pole to support an intravenous solution), a circuit mount or support arm (e.g., supporting a breathing circuit such as a tube from the ventilator 200 to a patient), a bar, a hook, a bed mount, a tray, or any other accessory as required or desired. The accessory mount 140 is coupled to the handgrip 130 so that the technologist can easily move (e.g., slide) the mount 140 around the handgrip 130 as required or desired. Additionally, the accessory mount 140 can be removed from the handgrip 130 without any tools by the technologist. In one example, the accessory mount 140 may include a clamp 150 to selectively secure the mount 140 to the handgrip 130 and lock the mount 140 in place. The accessory mount 140 is described further below in reference to FIG. 5.

Figure 3:
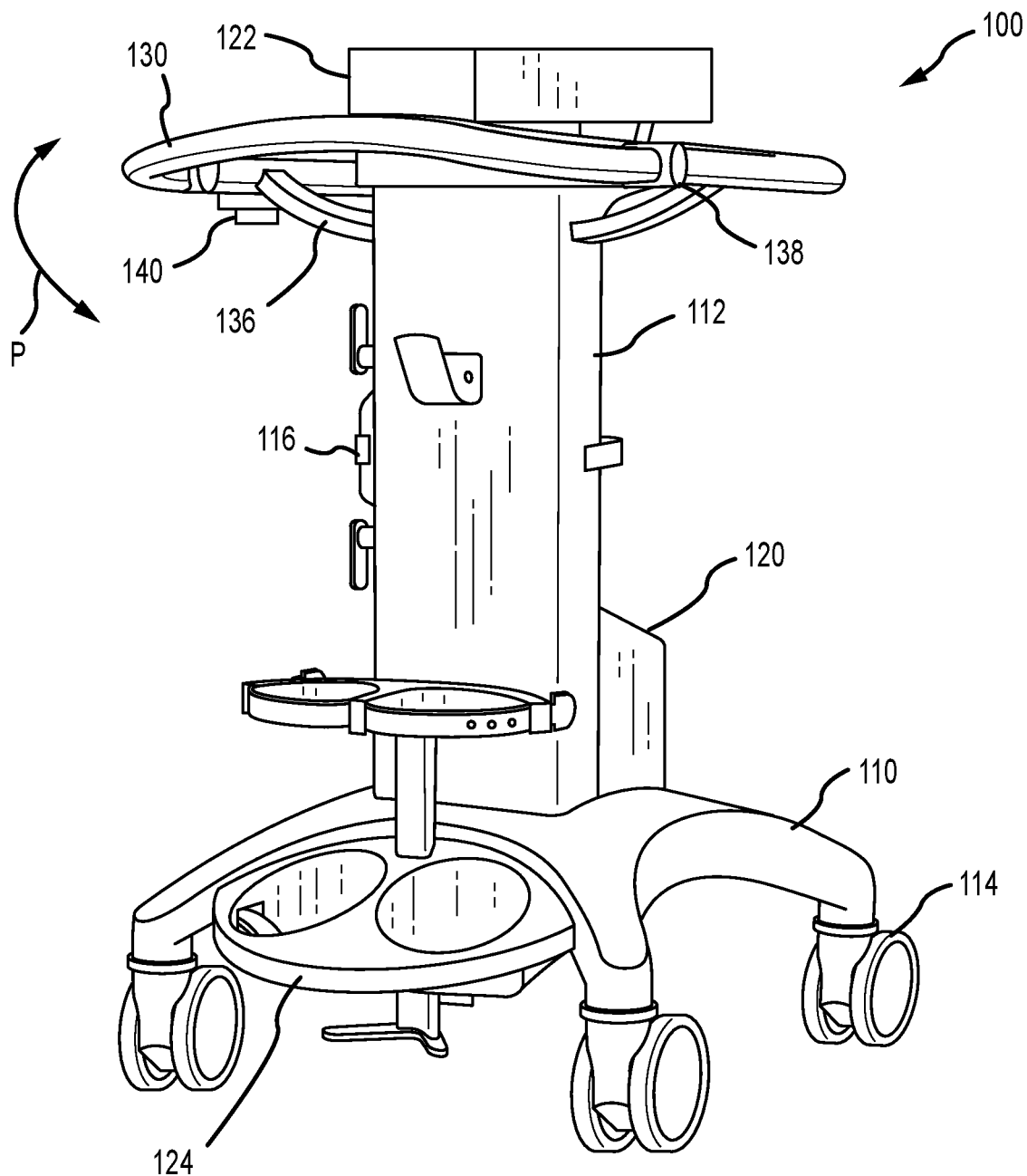
FIG. 3 is a rear perspective view of the cart shown in FIG. 1.

FIG. 2 is a front perspective view of the cart 100. FIG. 3 is a rear perspective view of the cart 100. Referring concurrently to FIGS. 2 and 3, the ventilator 200 (shown in FIG. 1) is not illustrated for clarity and certain components are described above, and thus, are not necessarily described further. On the rear side of the cart 100, the tank mount assembly 124 may be attached to the base 110 between two wheels 114. The tank mount assembly 124 is configured to hold one or two gas tanks 118 (shown in FIG. 1), such as, compressed air or oxygen. In the example, a portion of the handgrip 130 may extend above the tank mount assembly 124 and the gas cylinders so that the rear mounted cart components are prevented from being struck while moving the cart 100. However, this position of the handgrip 130 may restrict access to the tank mount assembly 124 (e.g., for mounting the gas cylinders to the cart 100). In another example, the gas cylinders may include regulators (not shown) and other accessories that the handgrip 130 restricts access to. As such, the handgrip 130 may include one or more pivot points 138 that enables a portion of the handgrip 130 to selectively pivot P relative to the column 112 and allow more access to the rear mounted cart components. In the example, the handgrip 130 can pivot in an upward direction from a horizontal plane. In other example, the handgrip 130 may pivot in a downward direction from the horizontal plane, or may even pivot in both an upward direction and a downward direction as required or desired.

In the example, one or more of the pivot points 138 may include a release button assembly that when depressed, allows the portion of the handgrip 130 between the pivot points 138 to pivot P (e.g., in a downward or an upward direction from horizontal). The release button assembly then can lock the handgrip 130 in place when it is pivoted back in line with the rest of the handgrip 130. In some examples, the release button assembly may lock the handgrip 130 in any angular position as required or desired. In other examples, the pivot points 138 may have any other structure that enables the function of the handgrip 130 as described herein.

Figure 4:
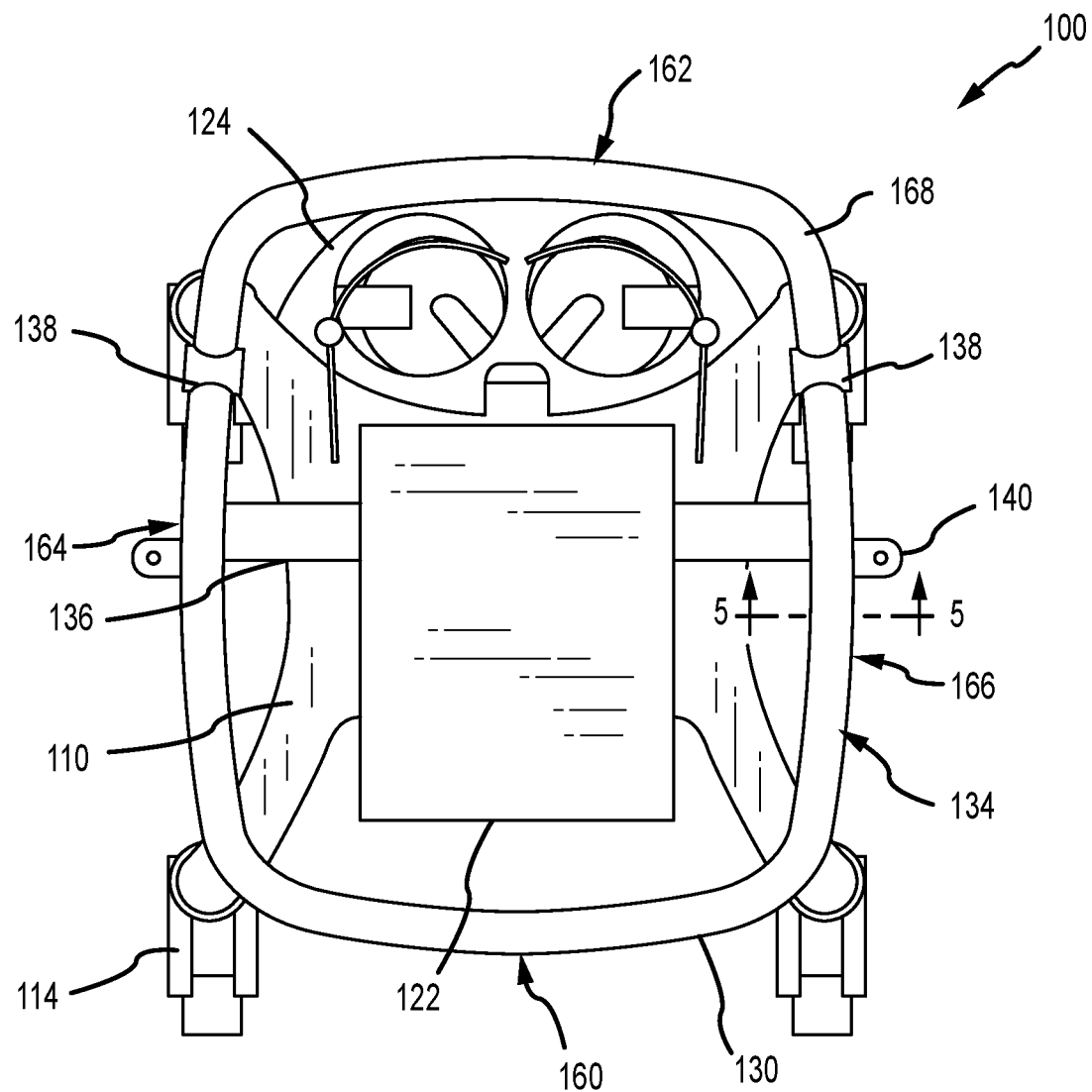
FIG. 4 is a top view of the cart shown in FIG. 1.

FIG. 4 is a top view of the cart 100. Certain components are described above, and thus, are not necessarily described further. In the example, the handgrip 130 encircles the cart 100, forming a closed loop around the platform 122. The handgrip 130 forms a continuous closed loop so that there is no open arm or end that can snag medical tubing or other lines. Additionally, the handgrip 130 may be substantially rectangular in shape with a front portion 160, a rear portion 162, and two side portions 164, 166 extending therebetween and coupled together via corners 168. In other examples, the shape of the handgrip 130 may be any other shape (e.g., circular, oval, polygonal, etc.) as required or desired.

The handgrip 130 has an upper surface 134 that is continuous and substantially uninterrupted along the entire length of the handgrip 130. For example, along the entire 360° around the cart 100. In an aspect, the handgrip 130 can be made by an additive manufacturing process (e.g., 3D printing), so as to provide a single piece that provides the smooth top surface. In examples, the upper surface 134 is continuous and uninterrupted along a discrete segment of the handgrip 130 (e.g., along the sides of the handgrip 130), and multiple segments may connect together at a seam to assemble the entire length of the handgrip 130 around the cart 100. The upper surface 134 is easy to clean by wiping and is substantially devoid of cracks or openings that could collect fluid or be difficult to clean.

Figure 5:
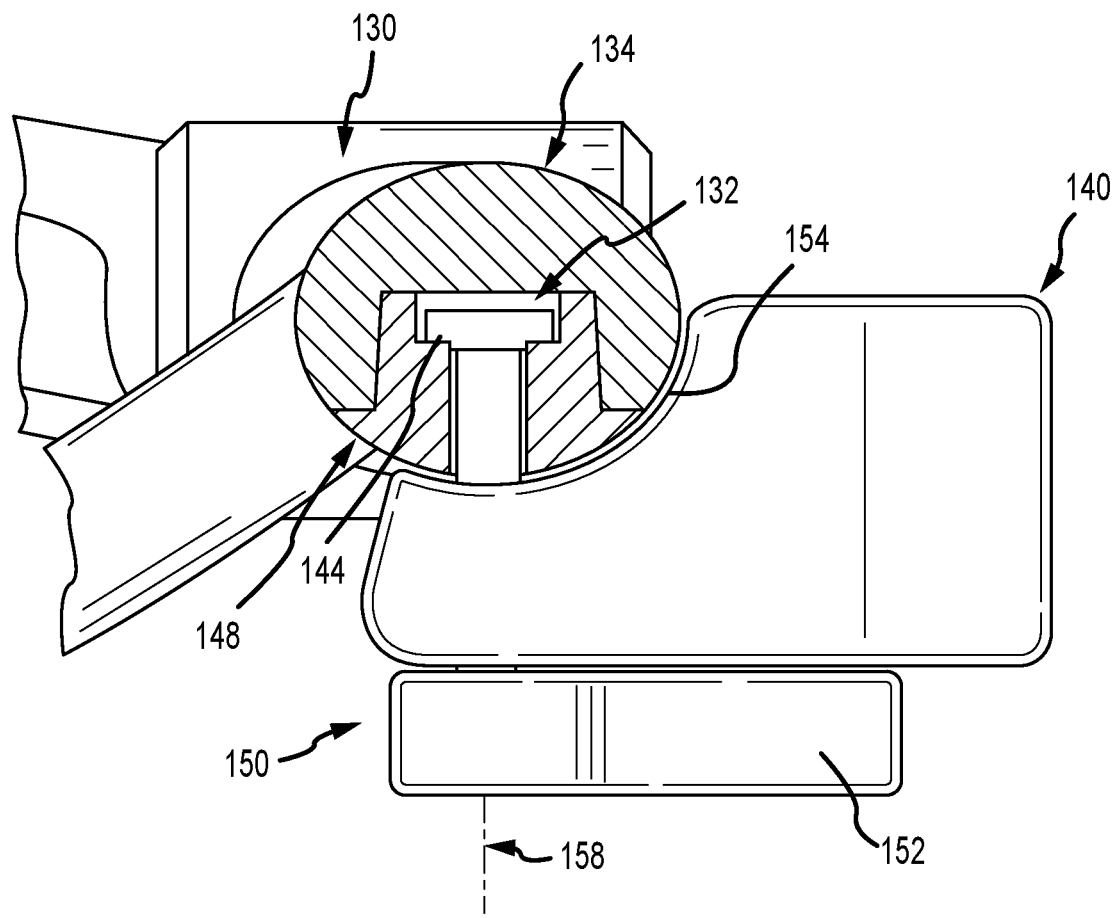
FIG. 5 is a cross-sectional view of a handgrip with an accessory mount taken along line 5-5 in FIG. 4.
Figure 7:
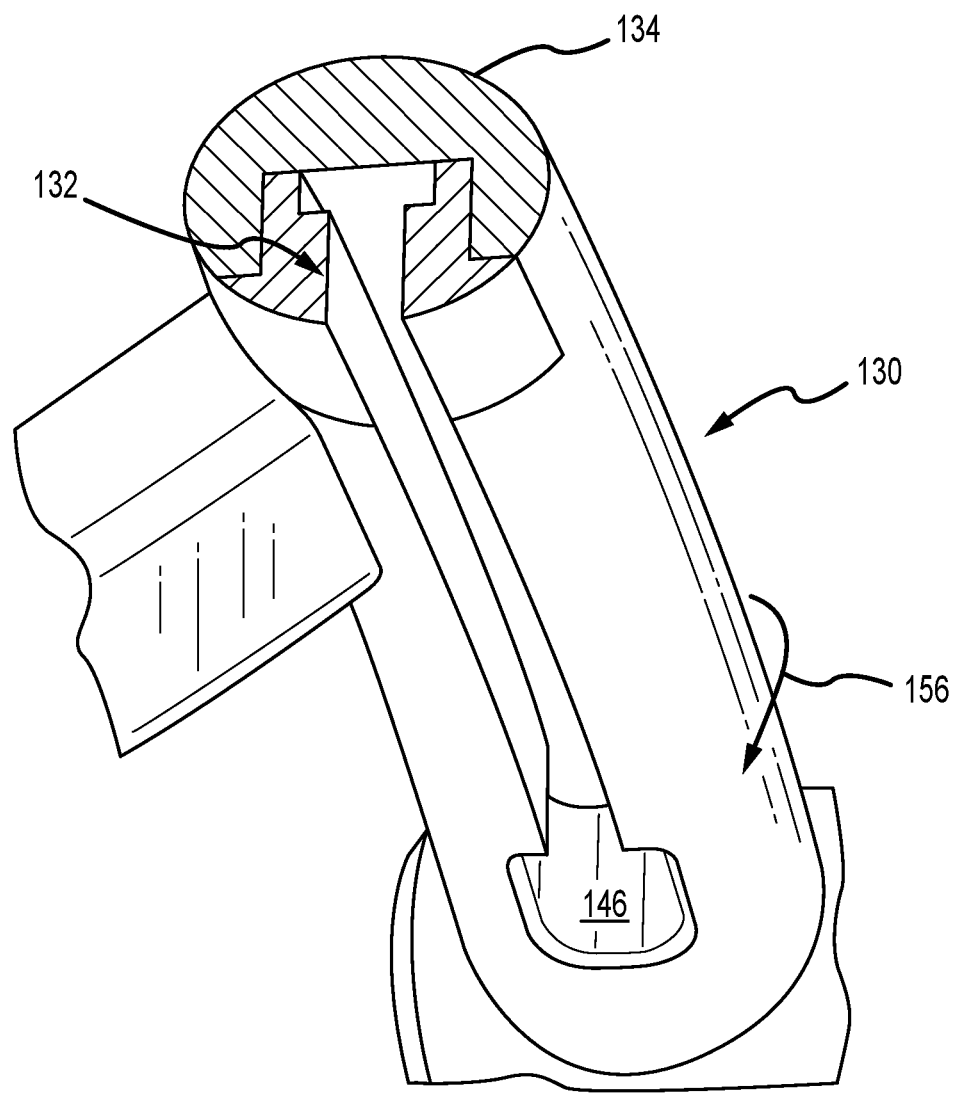
FIG. 7 is a partial bottom perspective view of the handgrip shown in FIG. 5.

Additionally, the handgrip 130 includes a lower surface 148 that has one or more elongated accessory slots 132 (both the lower surface 148 and the slot 132 are shown in FIGS. 5 and 7). The slot 132 is configured to receive a portion of the accessory mount 140 so that the mount 140 is slidingly adjustable along the length of the slot 132. The slot 132 is disposed on the underside of the handgrip 130, and extends along the handgrip 130 a sufficient distance to allow one or more accessory mounts 140 to be attached to the slot 132 and to allow the accessory mounts 140 to slide along the slot 132 to desired locations on the handgrip 130. As such, technologists have the flexibility to position medical accessories at any position along the handgrip 130, rather than being limited to positioning such accessories only at discrete mounting points on the handgrip 130.

Figure 8:
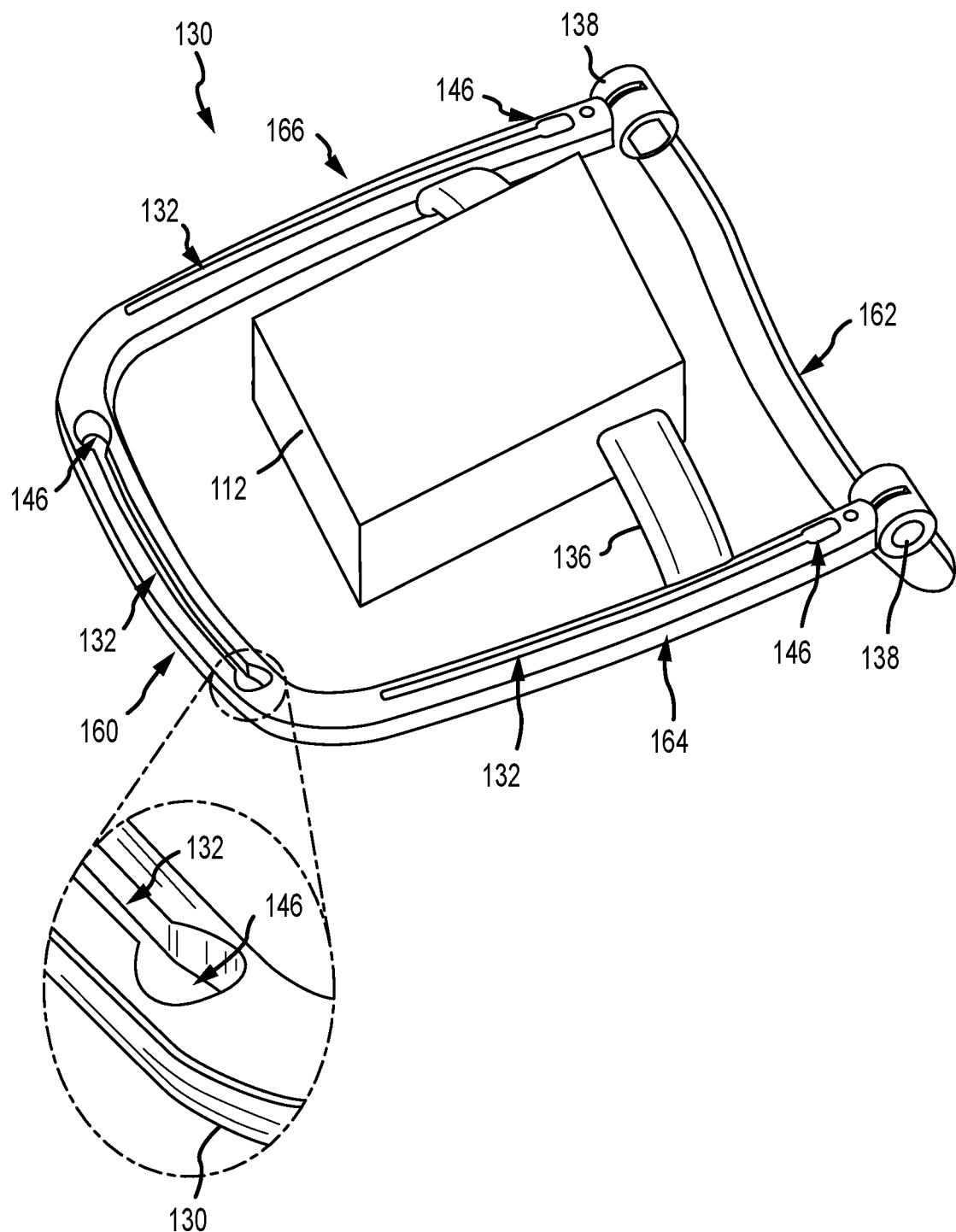
FIG. 8 is a bottom perspective view of the handgrip shown in FIG. 5.

In the example, the elongated accessory slot 132 includes three discrete slots, each disposed on separate sides of the handgrip 130, such as on the front portion 160 and the two side portions 164, 166 as shown in FIG. 8 and described below. This leaves the corners 168 of the handgrip 130 substantially devoid of the slots 132 because it is more difficult to slide the accessory mount 140 around the corners 168. In other examples, the rear portion 162 may include an accessory slot 132 as required or desired. In another example, a single slot may extend on the handgrip 130 all the way around the cart 100 (e.g., 360°) and including the corners 168. In some examples, the slot 132 may extend on the handgrip 130 about or more than half way around the cart 100 (e.g., 180°). In still other examples, the slot may extend on the handgrip 130 about three-quarters of the way around the cart (e.g., 270°). Additionally or alternatively, any number of slots 132 at any location on the handgrip 130 may be utilized as required or desired. For example, two or more slots can be provided without connecting to each other, such as two slots (e.g., on opposite sides or on the front and back of the handgrip 130), three slots, four slots, or any other number of individual slots, and any portion of the handgrip 130 may be formed without the slot on the underside. Because the slot 132 extends around the handgrip 130 at any number of required or desired locations, the accessory mount 140 can be positioned in various different desired positions along the handgrip 130 and can be moved to a new position if desired.

Figure 6:
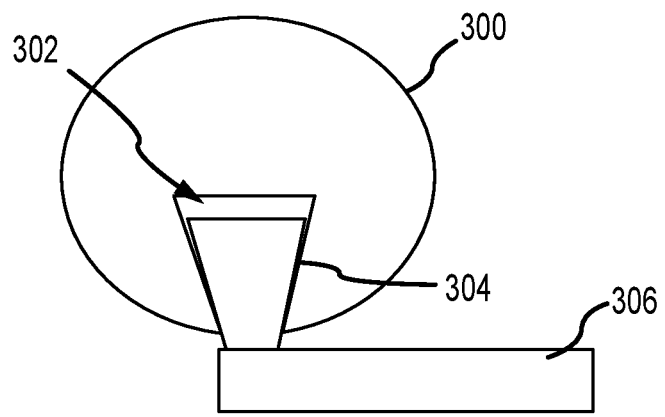
FIG. 6 is a cross-sectional view of another handgrip.

FIG. 5 is a cross-sectional view of the handgrip 130 with the accessory mount 140 taken along line 5-5 in FIG. 4. The elongated slot 132 may be formed on the underside of the handgrip 130 and opens downwardly toward the wheels 114 of the cart 100 (shown in FIGS. 1-3). The slot 132 is provided to attach one or more accessory mounts 140 to the handgrip 130. As depicted here, the slot 132 is a T-slot, meaning it has a T-shape in cross-section. In other examples, the slot 132 has any other suitable shapes that enables the handgrip 130 to function as described herein, such as a dovetail shape as shown in FIG. 6, a stepped shape, or a stepped or widened cross-section. The handgrip 130 also includes the smooth upper surface 134 that does not open into the slot 132. In the example, the upper surface 134 is continuous and uninterrupted, and because the slot 132 opens downwardly, the upper surface 134 does not collect water or other fluids. The upper surface 134 of the handgrip 130 can define a plane that is substantially parallel to the wheels of the cart. In some examples, the slot 132 may extend in a substantially orthogonal direction to this plane. In other directions, the slot 132 may be angled relative to this plane, but still open in a downwards direction so as to not collect water or other fluids.

In the example, the slot 132 has a shape (e.g., a T-shape as illustrated, a dovetail shape, a stepped or widened shape, or any other similar shape) that enables a portion of the accessory mount 140 to be retained in the slot 132, and thus, attach the mount 140 to the lower surface 148 of handgrip 130. Additionally, the slot 132 enables for the accessory mount 140 to longitudinally slide therein (e.g., in an out of the page) so that the accessory mount 140 can be moved to any location of the handgrip 130 of the cart. The accessory mount 140 itself supports various accessories, such as the pole 142 (shown in FIG. 1) to support an intravenous solution, a circuit mount or support arm (e.g., supporting a breathing circuit such as a tube from a ventilator to a patient), a bar, a hook, a bed mount, a tray, or any other accessory as required or desired. The accessory mount 140 may be shaped as a puck, block, bracket, or hub.

The accessory mount 140 includes a T-shaped nut or head 144 that fits into the T-shaped slot 132. The head 144 is sized and shaped to be complementary to the slot 132, so that the head 144 fits into the slot 132 and is retained inside the slot 132 (e.g., vertically), while still enabling sliding movement of the head 144 along the slot 132. In one example, the head 144/slot 132 coupling can support at least 50-pounds of accessories on the accessory mount 140. The head 144 and the slot 132 have a complementary shape that retains the head 144 within the slot 132, such as the head 144 having a portion that is wider than a relatively narrower opening of the slot 132. The fitting between the head 144 and the slot 132 frees the mount 140 itself to take on any suitable or desirable shape, unconstrained by the shape of the slot 132. With the head 144 retained by the slot 132, the rest of the mount 140 can embody a wide variety of shapes or sizes as needed for a particular medical environment.

In the example, the accessory mount 140 includes a clamp 150 with a knob or key 152. The key 152 is actuatable, such as by rotating about a rotation axis 158, to release or tighten the clamp 150. The rotation axis 158 may be substantially parallel to the head 144. When tightened, the clamp 150 locks the accessory mount 140 against the handgrip 130 to fix and secure the mount 140 in position and prevent it from sliding along the slot 132. In this locked position (as shown in FIG. 5), at least a portion of the accessory mount 140 is pressed (e.g., frictionally engaged) against the handgrip 130 at one more points of contact. For example, the head 144 can pressed against a wall of the slot 132 and/or a surface 154 of the accessory mount 140 is pressed against the handgrip 130. When the accessory mount 140 is locked, the mount 140 is restricted from moving relative to the handgrip 130. Upon release of the clamp 150, the accessory mount 140 at least partially disengages with the handgrip 130 and loosens therefrom. This disengagement away from the handgrip 130 enables the accessory mount 140 to slide along the slot 132 to a new position as required or desired.

The clamp 150 can use a cam lock or other quick release mechanism to tighten and loosen against the handgrip 130. In the example, the clamp 150 is biased into the tightened position, such as by a spring, so that when the key 152 is released, the clamp 150 automatically returns to the tightened position to lock the accessory mount 140 in place. This prevents the accessory mount 140 from being left loose inadvertently and undesirably moving around the handgrip 130. In some examples, the accessory mount 140 includes the curved surface 154 that is shaped to match an outer profile of the handgrip 130. When the clamp 150 is tightened, the curved surface 154 contacts and presses against the outer surface of the handgrip 130. In an example, this aligned curvature helps with smooth tracking along the handgrip 130 and improves weight loading by distributing load across the handgrip 130 instead of only at the slot 132.

In the example, the handgrip 130 may be a two piece construction so as to increase the structural rigidity of the handgrip 130. A lower portion of the handgrip 130 may be formed from a stiff, high density, and/or high strength material. This enables for the slot 132 to be formed therein and provide the structural rigidity for the accessory mount 140 to be coupled thereto. An upper portion of the handgrip 130 may be formed from a lighter weight material that provides a continuous, uninterrupted, and smooth top surface. The slot 132 may open from the handgrip 130 substantially parallel to the vertical (e.g., top-bottom) direction. In other example, the slot 132 may open from the handgrip 130 at an acute angle from the vertical direction. However, the slot 132 still opens in a downward direction so that water or other fluids are not collected therein.

FIG. 6 is a cross-sectional view of another handgrip 300. In this example, an elongated accessory slot 302 is substantially dovetail-shaped and configured to receive a corresponding head 304 of an accessory mount 306. When the head 304 is engaged in the slot 302, the enlarged portion of the head 304 retains the accessory mount 306 in the slot 302. Similar to the example described above, the head 304 fits into the slot 302 and is retained inside the slot 302 (e.g., vertically), while still enabling sliding movement of the head 304 along the slot 302.

Turning back to the example of the cart 100 shown in FIGS. 1-5, FIG. 7 is a partial bottom perspective view of the handgrip 130. In the example, the slot 132 extends along the handgrip 130 for a length as required or desired. In some examples, the slot 132 can have enough length to accommodate more than one accessory mount 140 (shown in FIG. 5). The slot 132 can have either a linear or a curved shape as it extends around the handgrip 130, or can rise up or down, such as following a curved contour of the handgrip as shown in FIGS. 1-3. Additionally, the slot 132 is not limited to being linear, straight, or flat. When the slot 132 has a curved shape, the slot 132 is large enough so that the head 144 of the accessory mount 140 can navigate around the curve in the slot 132.

In the example, the accessory mount 140 is removably inserted within the slot 132 and to couple the mount 140 to the handgrip 130, the head 144 can be inserted into the slot 132 at an opening 146. The opening 146 is an enlarged access to the slot 132, enabling the head 144 to enter or exit the slot 132. The accessory mount 140 can then slide along the slot 132 to a desired position along the handgrip 130 as described herein. The opening 146 is configured to direct the portion of the accessory mount 140 into the slot 132. In some examples, the opening 146 may be substantially tapered to assist directing the head 144 towards the slot 132. For example, the opening 146 is sized and shaped to self-align the head 144 with the slot 132 so that the accessory mount 140 can be attached without direct line of sight of the opening 146 and/or slot 132, which may occur because the opening 146 and the slot 132 are on the underside of the handgrip 130. In one example, the opening 146 may be substantially circular that tappers towards the slot 132.

The slot 132 may have more than one opening 146, so that the accessory mount 140 can be attached or removed from the handgrip 130 at more than one position. For example, the slot 132 may include two openings 146 at opposite ends of the elongated slot 132. As a result, an accessory mount that is far from a first opening can be removed at a second opening, without needing to remove other accessory mounts between it and the first opening. Similarly, new accessory mounts can be added at one side of the slot 132 without disturbing the accessory mounts on the other side. In some examples, the opening 146 may be located at a middle location of the slot 132 and between the ends as required or desired. In another example, the opening 146 may be positioned at the right and left front corners of the handgrip 130.

Since the opening 146 and the slot 132 are on the underside of the handgrip 130, to assist the technologist with locating the openings 146, one or more indicia 156 may be placed on the upper surface 134 of the handgrip 130. The indicia 156 can be an arrow pointing to the location of the opening 146. In other examples, the indicia 156 can be a symbol, a letter, a word, raised notches, or any other visual or physical indicators that identify the location of the opening 146. In some examples, the indicia 156 may be color coded (e.g., the beginning or end opening of the slot) as required or desired.

FIG. 8 is a bottom perspective view of the handgrip 130 shown in FIG. 5. Certain components are described above, and thus, are not necessarily described further. The rear portion 162 of the handgrip 130 is shown in a pivoted configuration (e.g., in an upward direction) and enabled by the pivot points 138. Additionally, three discrete slots 132 are formed in the handgrip 130. One slot 132 on each side portion 164, 166, and a slot 132 on the front portion 160. In the example, the slots 132 on the side portions 164, 166 include the opening 146 that is disposed proximate the pivot points 138. These slots 132 may only include the single opening 146. The slot 132 on the front portion 160 includes two openings 146, one on each end of the slot 132. The openings 146 are substantially oval in shape with the slot 132 beginning at one end of the major axis. As such, the sidewalls of the opening 146 are not undercut so that the head 144 of the accessory mount 140 (shown in FIG. 5) may be self-directed towards the slot 132. Additionally, the curved oval shape of the opening 146 also directs the head towards the slot 132 for engagement therebetween. In the example, the sidewalls of the opening 146 are substantially normal to the inner surface of the slot 132. In other examples, one or more of the sidewalls of the opening 146 may be tapered (e.g., sloped) towards the slot 132.

Numerous changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the disclosure. Numerous other changes may be made which will readily suggest themselves to those skilled in the art and which are encompassed in the spirit of the disclosure and as defined in the claims.

What is claimed is:

1. A medical equipment cart, comprising:
   a handgrip at least partially encircling a portion of the medical equipment cart, wherein the handgrip comprises:
   an upper surface substantially devoid of openings; and
   an opposite lower surface comprising an elongated accessory slot opening downwardly, wherein the elongated accessory slot is configured to receive a portion of an accessory mount such that the accessory mount is slidingly adjustable along a length of the elongated accessory slot.

2. The medical equipment cart of claim 1, wherein the accessory slot is substantially T-shaped.

3. The medical equipment cart of claim 1, wherein the accessory slot is substantially dovetail-shaped.

4. The medical equipment cart of claim 1, wherein an end of the accessory slot includes an enlarged opening, wherein the enlarged opening is configured to direct a portion of the accessory mount into the accessory slot.

5. The medical equipment cart of claim 4, wherein the enlarged opening is substantially tapered.

6. The medical equipment cart of claim 1, wherein the handgrip comprises an unbroken loop around the portion of the cart.

7. The medical equipment cart of claim 6, wherein a portion of the handgrip is devoid of the accessory slot.

8. The medical equipment cart of claim 6, wherein the handgrip is substantially rectangular and two opposing sides comprise a pivot point so that a portion of the handgrip may selectively pivot relative to a column.

9. A cart for a medical ventilator, comprising:
   a handgrip encircling a platform in an unbroken loop, wherein the handgrip comprises:
   an upper surface; and
   an opposite lower surface comprising an elongated accessory slot opening downwardly; and
   an accessory mount comprising a head, wherein the head is at least partially receivable within the elongated accessory slot such that the accessory mount is slidingly adjustable along a length of the accessory slot.

10. The cart of claim 9, wherein the accessory mount comprises a clamp for selectively locking the accessory mount to the handgrip.

11. The cart of claim 10, wherein the clamp is biased toward a tightening configuration to lock the accessory mount to the handgrip.

12. The cart of claim 9, wherein the accessory mount supports a circuit support arm.

13. The cart of claim 9, wherein the elongated accessory slot comprises an enlarged opening configured to receive the head so that the head can be disposed within the elongated accessory slot.

14. The cart of claim 13, wherein the upper surface comprises an indicia that corresponds to a position of the enlarged opening.

15. A handgrip assembly for a medical equipment cart, comprising:
   a substantially rectangular shaped handgrip that at least partially encircles an upper portion of the medical equipment cart, the handgrip comprising:
   an upper surface substantially devoid of openings; and
   an opposite lower surface comprising at least two discrete elongated accessory slots opening in a downward direction;
   an accessory mount comprising a head, wherein the head is at least partially receivable within each of the at least two discrete elongated accessory slots such that the accessory mount is slidingly adjustable along a length of one of the at least two discrete elongated accessory slots.

16. The handgrip assembly of claim 15, wherein one of the at least two discrete elongated accessory slots extends around the handgrip for at least 180°.

17. The handgrip assembly of claim 15, wherein one of the at least two discrete elongated accessory slots is T-shaped.

18. The handgrip assembly of claim 15, wherein corners of the handgrip are devoid of the at least two discrete elongated accessory slots.

19. The handgrip assembly of claim 15, wherein each of the at least two discrete elongated accessory slots comprises at least one enlarged opening configured to receive the head so that the head can be disposed within the at least two discrete elongated accessory slots.

20. The handgrip assembly of claim 15, wherein each end of the at least two discrete elongated accessory slots comprises an enlarged opening configured to receive the head so that the head can be disposed within the at least two discrete elongated accessory slots.

* * * * *